(12) United States Patent
Silver

(10) Patent No.: US 6,497,677 B2
(45) Date of Patent: Dec. 24, 2002

(54) MANUAL BREASTMILK PUMP

(75) Inventor: Brian H. Silver, Cary, IL (US)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 09/947,135

(22) Filed: Sep. 5, 2001

(65) Prior Publication Data

US 2002/0032404 A1 Mar. 14, 2002

Related U.S. Application Data

(62) Division of application No. 09/505,319, filed on Feb. 16, 2000, now Pat. No. 6,299,594, which is a division of application No. 08/931,316, filed on Sep. 16, 1997, now Pat. No. 6,110,140.
(60) Provisional application No. 60/026,221, filed on Sep. 17, 1996.

(51) Int. Cl.$^7$ ................................. A61M 1/06
(52) U.S. Cl. ....................................... 604/74
(58) Field of Search ............... 604/73–76, 184, 604/346, 313–316, 30, 32, 33, 35, 118, 119, 248, 249, 220, 283; D24/109, 113–115; 119/14.01, 14.05, 14.22, 14.23, 14.24, 14.44; 251/207, 208, 210, 343–345; 137/853; 285/7

(56) References Cited

U.S. PATENT DOCUMENTS

| | | |
|---|---|---|
| 1,228,451 A | 6/1917 | Latts |
| 1,509,226 A | 9/1924 | Brown |
| 1,805,675 A | 5/1931 | Rudolph |
| 2,419,795 A | 4/1947 | Saunders .................... 128/297 |
| 2,539,846 A | 1/1951 | Lewis et al. ................... 604/74 |
| 2,712,950 A | 7/1955 | Siebert .......................... 285/7 |
| 2,760,754 A | 8/1956 | Gladstone |
| 3,033,226 A | 5/1962 | Allen .......................... 251/345 |
| 3,472,488 A | 10/1969 | Hastings ..................... 251/344 |
| 3,642,249 A | 2/1972 | Cruise ......................... 261/342 |
| 3,782,385 A | 1/1974 | Loyd ............................ 128/281 |
| 3,977,405 A | 8/1976 | Yanase ......................... 128/281 |
| 4,249,481 A | 2/1981 | Adams ...................... 119/14.02 |
| 4,263,912 A | 4/1981 | Adams ......................... 128/281 |
| 4,311,141 A | 1/1982 | Diamond ..................... 128/281 |
| 4,323,067 A | 4/1982 | Adams ......................... 128/281 |
| 4,466,461 A | 8/1984 | Weiss .......................... 251/344 |
| 4,573,969 A | 3/1986 | Schlensog et al. ............. 604/74 |
| 4,583,970 A | 4/1986 | Kirchner ....................... 604/74 |
| 4,673,388 A | 6/1987 | Schlensog et al. ............. 604/74 |
| 4,758,232 A | 7/1988 | Chak ........................... 604/220 |
| 4,759,747 A | 7/1988 | Aida et al. ..................... 604/74 |

(List continued on next page.)

FOREIGN PATENT DOCUMENTS

| | | | |
|---|---|---|---|
| CH | 251810 | 9/1948 | |
| DE | 87 14 995.8 | 11/1987 | ............ A61M/1/06 |
| EP | 0 162 358 | 11/1985 | ............ A61M/1/06 |
| EP | 0 733 376 A2 | 9/1996 | ............ A61M/1/00 |
| GB | 185521 | 9/1922 | |
| GB | 271857 | 10/1927 | |
| GB | 762701 | 12/1956 | |
| GB | 2 127 293 A | 4/1984 | ............ A61M/1/06 |
| IT | 407293 | 12/1946 | |

OTHER PUBLICATIONS

Lawrence, Ruth A., M.D., Breastfeeding: A Guide for the Medical Profession.
Medela Hospital Catalog, 1992.
Specification, MEDAP Milchsauger P 6010.

Primary Examiner—Sharon Kennedy
(74) Attorney, Agent, or Firm—Baniak Pine & Gannon

(57) ABSTRACT

An easy to assemble breastmilk pump with an effective and easy to operate manual pumping mechanism that allows in one aspect for one-handed or two-handed operation, a novel piston pump mechanism in another aspect of the invention, an improved vacuum regulator in yet another aspect that can be easily adjusted during operation, and a locking mechanism in still another aspect to prevent accidental disengagement of the reciprocating parts during operation.

11 Claims, 8 Drawing Sheets

U.S. PATENT DOCUMENTS

| | | |
|---|---|---|
| 4,772,262 A | 9/1988 | Grant et al. ............... 604/74 |
| 4,799,922 A | 1/1989 | Beer et al. ................ 604/74 |
| 4,813,932 A | 3/1989 | Hobbs ..................... 604/74 |
| 4,857,051 A | 8/1989 | Larsson ................... 604/74 |
| 4,883,464 A | 11/1989 | Morifuki .................. 604/74 |
| 4,886,494 A | 12/1989 | Morifuji ................... 604/74 |
| 4,892,517 A | 1/1990 | Yuan et al. ............... 604/74 |
| 4,929,229 A | 5/1990 | Larsson ................... 604/74 |
| 4,964,851 A | 10/1990 | Larsson ................... 604/74 |
| 5,007,899 A | 4/1991 | Larsson ................... 604/74 |
| 5,009,638 A | 4/1991 | Riedweg et al. .......... 604/74 |
| 5,071,403 A | 12/1991 | Larsson ................... 604/74 |
| 5,295,957 A | 3/1994 | Aida et al. ................ 604/74 |
| 5,749,850 A | 5/1998 | Williams et al. .......... 604/74 |
| 5,784,750 A | 7/1998 | Sankovic et al. ........... 285/7 |
| 6,110,140 A | 8/2000 | Silver ...................... 604/74 |
| 6,299,594 B1 | 10/2001 | Silver ...................... 604/74 |

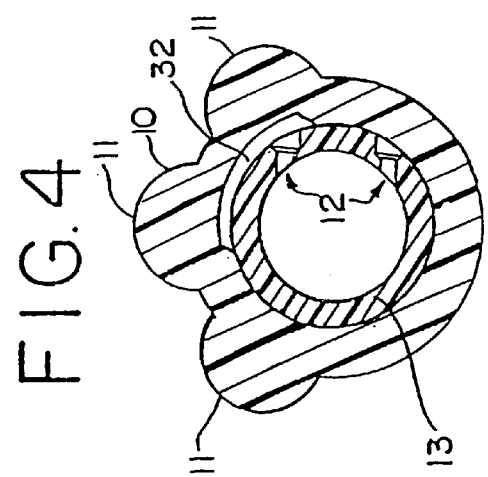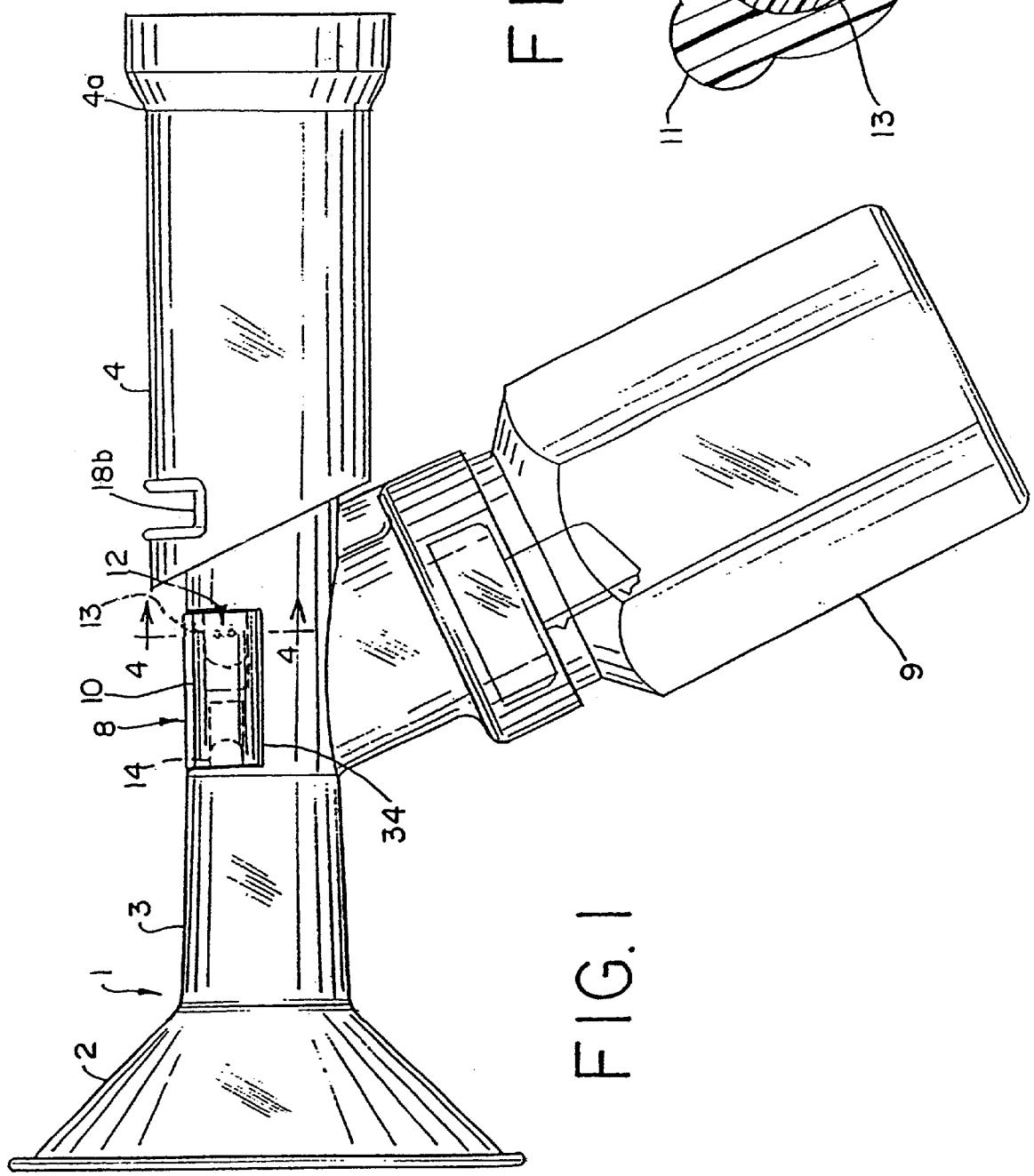

MANUAL BREASTMILK PUMP

This application is a divisional of application Ser. No. 09/505,319, filed on Feb. 16, 2000, now U.S. Pat. No. 6,299,594, which is a divisional of prior application Ser. No. 08/931,316, filed on Sep. 16, 1997, now U.S. Pat. No. 6,110,140, which claims benefit of Provisional Application Serial No. 60/026,221, filed on Sep. 17, 1996.

FIELD OF THE INVENTION

The present invention generally relates to breastmilk pumps, and more particularly relates to a new and improved breastmilk pump with an effective and easy to operate manual pumping mechanism, a mechanism for one-handed or two-handed operation, and an improved vacuum regulator.

BACKGROUND OF THE INVENTION

Breastmilk pumps are well known and generally comprise a hood body or breast shield that fits over the breast, a vacuum pump connected to the hood body for generating an intermittent reduced pressure or vacuum within the hood body, and a receptacle for the expressed milk. Examples of these pumps are shown in U.S. Pat. Nos. 4,857,051 and 4,964,851.

An aspect of the design of a manually driven pump has been the amount of effort required to use the pump. As the user's hand tired, the suction created may decrease, as well as the stroke rate, thus decreasing the effectiveness of the pumping action. Manufacturing costs have also been a consideration because of numerous pieces that may be required in the construction of these pumps. Regulating the vacuum pressure created by the pumping action is also a consumer design consideration. Solutions to these problems are presented in this invention as are other innovations.

SUMMARY OF THE INVENTION

The present invention has a principal objective of providing a manual pump that is easy to operate. In one embodiment, vacuum is created by sliding a closed-end cylinder over a pump tube extending from the hood body. The user grasps the outer circumference of the cylinder and gently glides the cylinder over the pump tube. This pumping design is considered easier to manipulate than the traditional design of a movable piston rod reciprocating within a stationary cylinder. As applied to an inventive breast pump, the user generates reduced pressure or vacuum with a simple, nonstressful hand movement which utilizes better-suited muscle groups for pumping.

In addition, a locking means has been developed to prevent the cylinder from disengaging from the pump tube after reaching the position which generates the maximum reduced pressure (maximum stroke). The locking means is simple to engage or disengage, such as for cleaning of the pump elements.

Another objective of this invention is to provide an improved mechanism for regulating the vacuum created by the pumping action, which mechanism can be manipulated during use to adjust the amount of suction generated by a pumping stroke. One aspect of the present invention is having the regulator on the breast pump unit adjacent the hood body. A rotary member with an internal groove or passage communicating with the atmosphere connects to a ported structure and rotates about the structure to regulate the reduced pressure generated, by variously exposing the ports to ambient air. The reciprocating action of the cylinder over the pump tube then draws a predetermined amount of air through one or more of the ports to modify the amount of vacuum.

Also, while one of the goals of this invention is to provide a user with a handy, low-cost, low maintenance manual pump, aspects of this invention can be further modified to allow use with motor driven pumps.

In another embodiment of the invention, a lever drive mechanism is added to a piston-type pump configuration, which has a movable piston rod inside a stationary cylinder. The lever arrangement allows a user to operate the pump with one hand by grasping the lever and piston cylinder in one hand. As the lever is moved toward the cylinder, the piston rod slides toward the rear of the cylinder under action from the lever, creating a negative pressure in the pump. A spring action to return the lever, and the piston rod, to the starting position when the user releases the lever, can also advantageously be added. The relative position of the pump and lever makes the pump easy to operate and maintain its position on the breast.

In another aspect of the invention, a breast pump is adapted for use with one or both hands. Using the foregoing embodiment having the lever mechanism for one-handed operation as an example, the piston is provided with a handgraspable part that extends out of the pump cylinder. The hand-graspable part can be reciprocated independently of the lever mechanism for two-handed operation. One-handed operation is provided by the lever mechanism, and another two-handed mode is provided by holding the pump in place with one hand and reciprocating the piston with the hand graspable part of the piston rod.

BRIEF DESCRIPTION OF THE DRAWINGS

FIG. 1 is a side elevational view showing a first embodiment of an improved breast pump made in accordance with the present invention, with the cylinder engaged over the pump tube;

FIG. 4 is an enlarged sectional view of the vacuum regulator taken along line 4—4 of FIG. 1;

DETAILED DESCRIPTION OF EMBODIMENTS OF THE INVENTION

Figure 2:
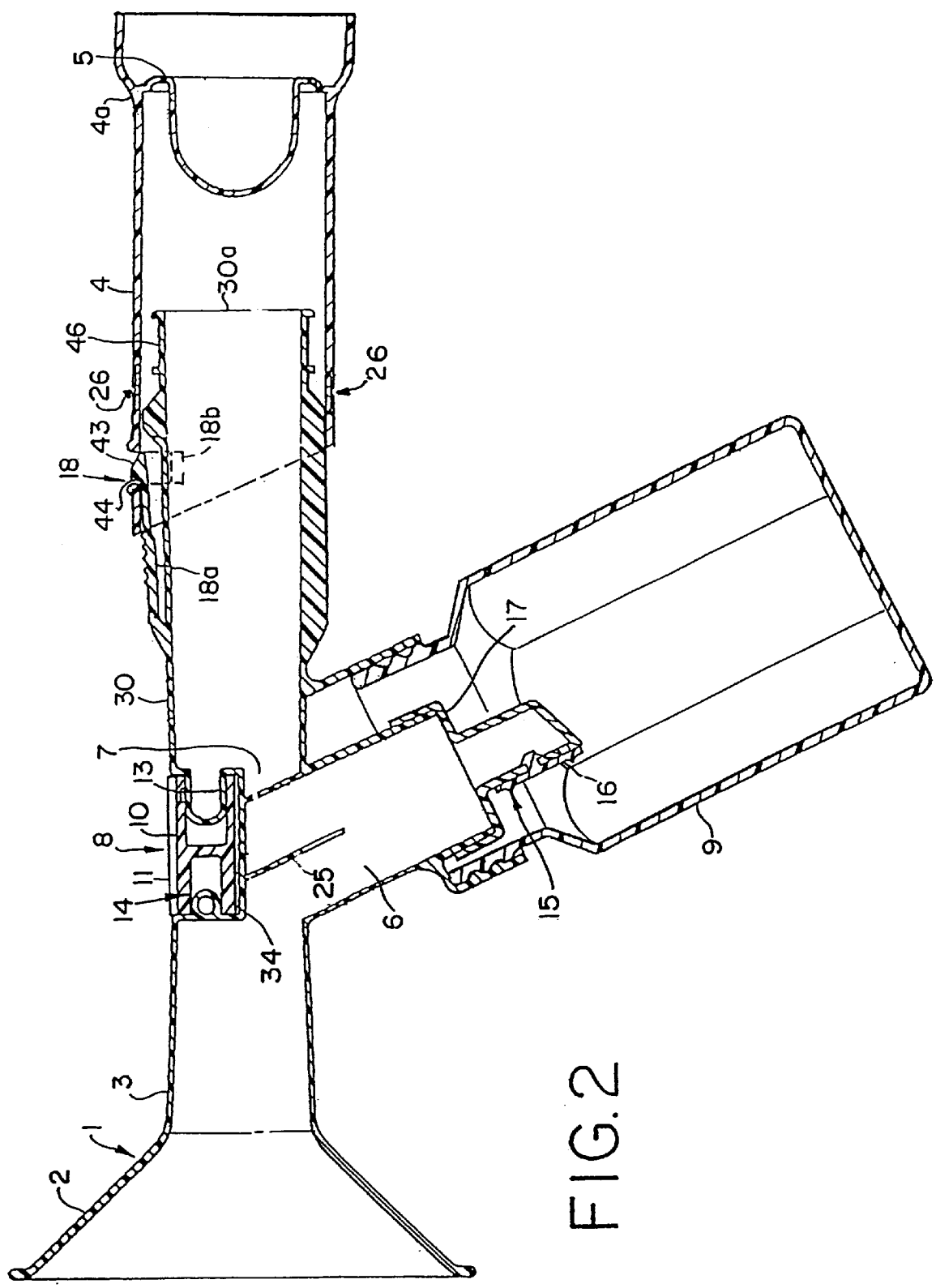
FIG. 2 is a sectional view of the embodiment of FIG. 1 with the cylinder reciprocated toward the rear end of the pump tube.
Figure 7:
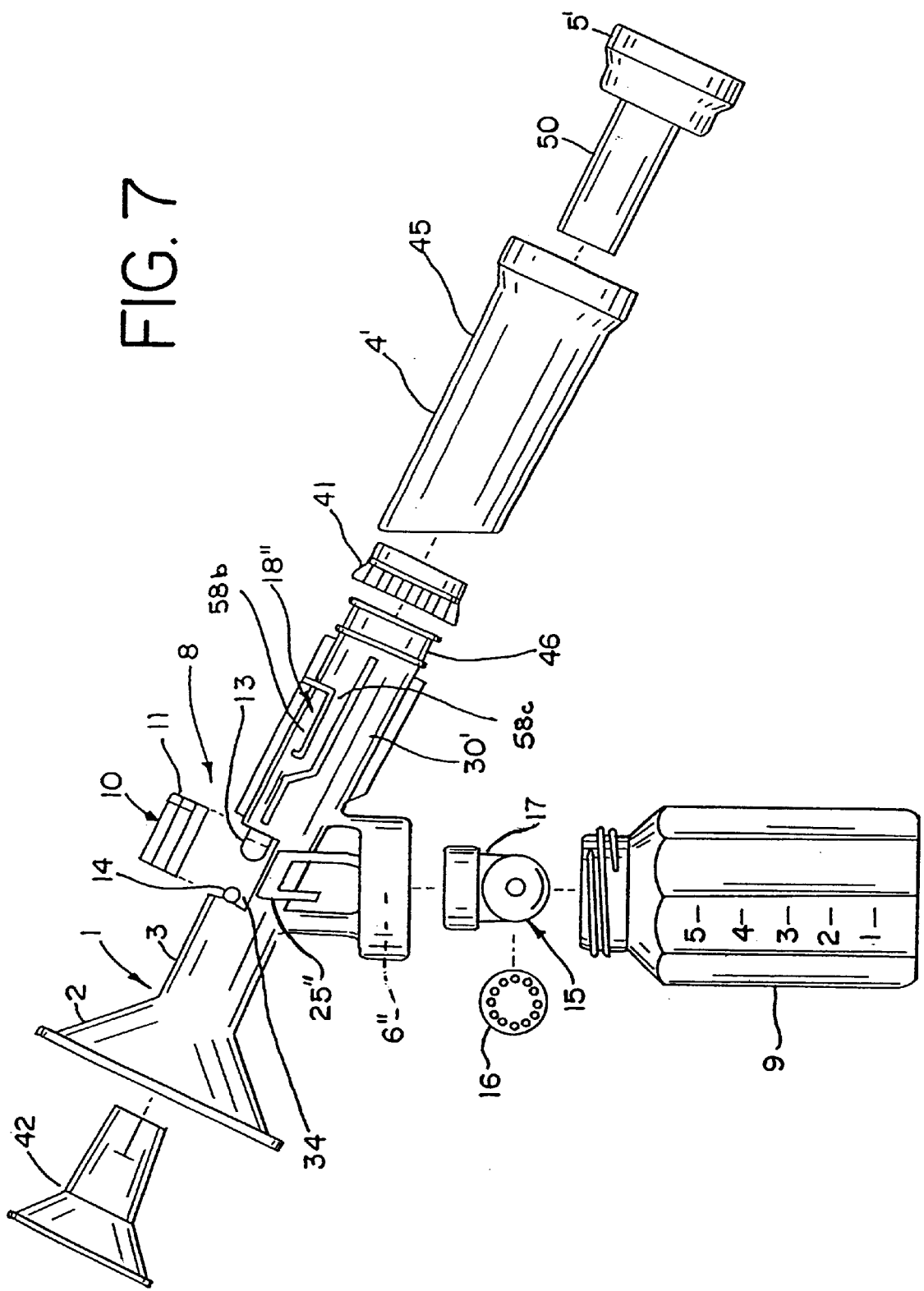
FIG. 7 is a side elevational view showing a third embodiment of an improved breast pump made in accordance with the present invention, showing the various parts comprising the breast pump.
Figure 8:
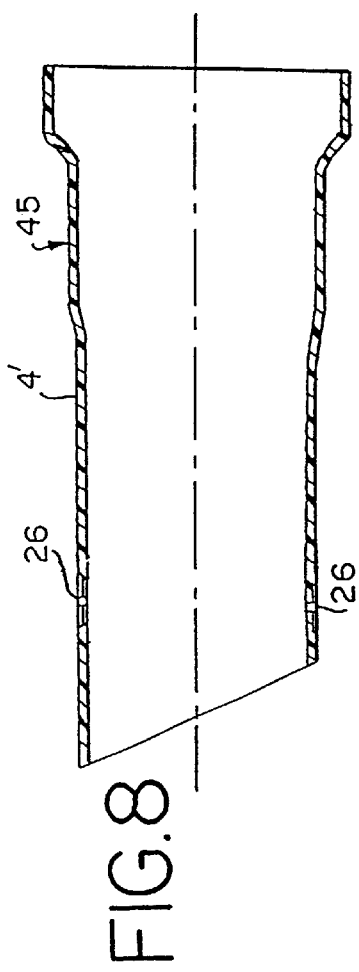
FIG. 8 is a sectional view of the cylinder of the third embodiment.
Figure 9:
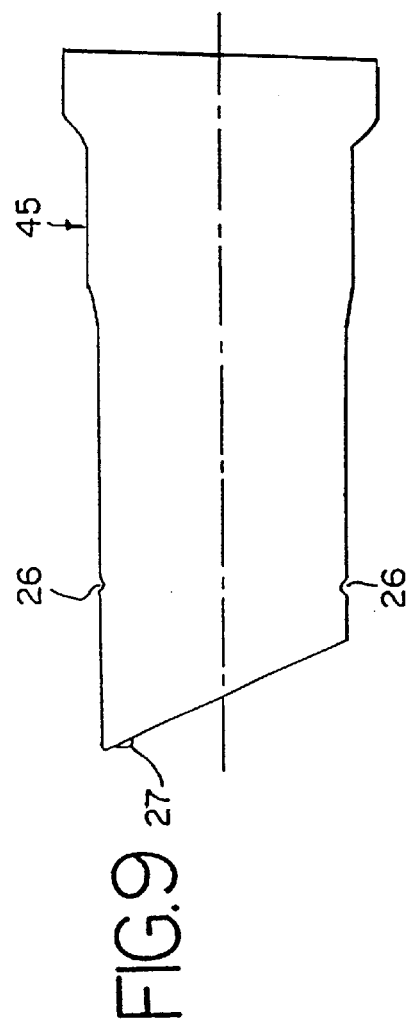
FIG. 9 is a side view of the cylinder of the third embodiment.
Figure 10:
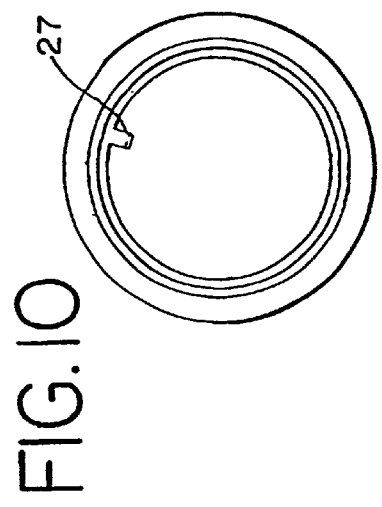
FIG. 10 is a frontal view of the cylinder of FIG. 9 showing the post extending downwardly therefrom.
Figure 11:
FIG. 11 is an enlarged sectional view of the post taken along line A—A of FIG. 10.
Figure 12:
FIG. 12 is a bottom view of the post of FIG. 11.
Figure 13:
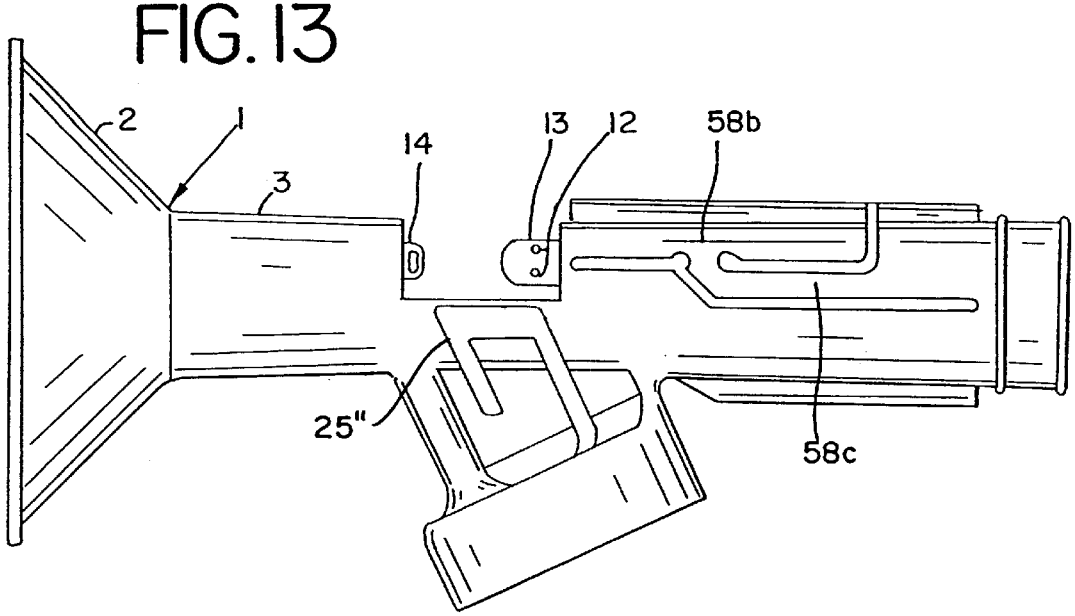
FIG. 13 is an enlarged side elevational view of the pump tube and additional elements of FIG. 7.
Figure 14:
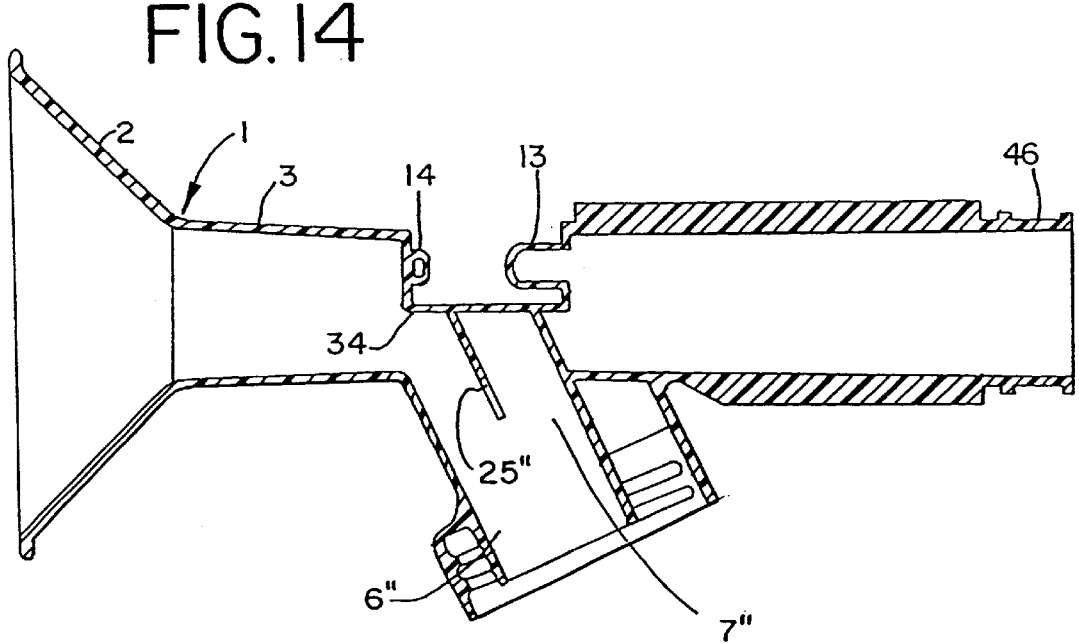
FIG. 14 is a sectional view of the embodiment depicted in FIG. 13.
Figure 15:
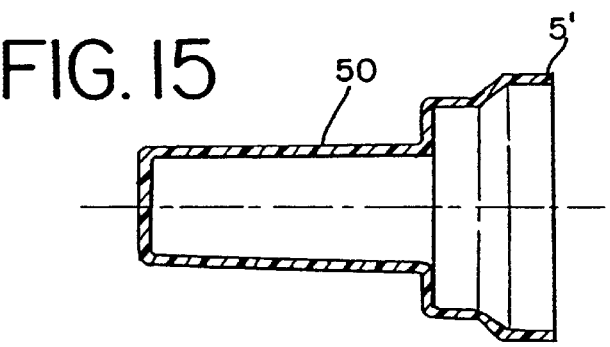
FIG. 15 is an enlarged sectional view of the end piece depicted in FIG. 7.

A first embodiment of a manually operable breast pump, as shown in FIGS. 1–4, has a hood body or shield 1 having two sections: a funnel shaped front section 2 and a tubular extension 3 extending therefrom. A vacuum regulator 8 is positioned on the hood body 1. A cylinder 4 has an end cap 5. The cylinder 4 is slidably engaged over a pump tube 30. When the cylinder 4 is reciprocated to the rear end 30a of the pump tube 30, as depicted in FIG. 2, reduced pressure or vacuum is created. A suitable substantially airtight engagement between the cylinder 4 and the pump tube 30 is provided as by a sliding interference-type fit, or a gasket or the like. The gasket (such as gasket 41 shown in FIG. 7) fits in annular groove 46.

Figure 3:
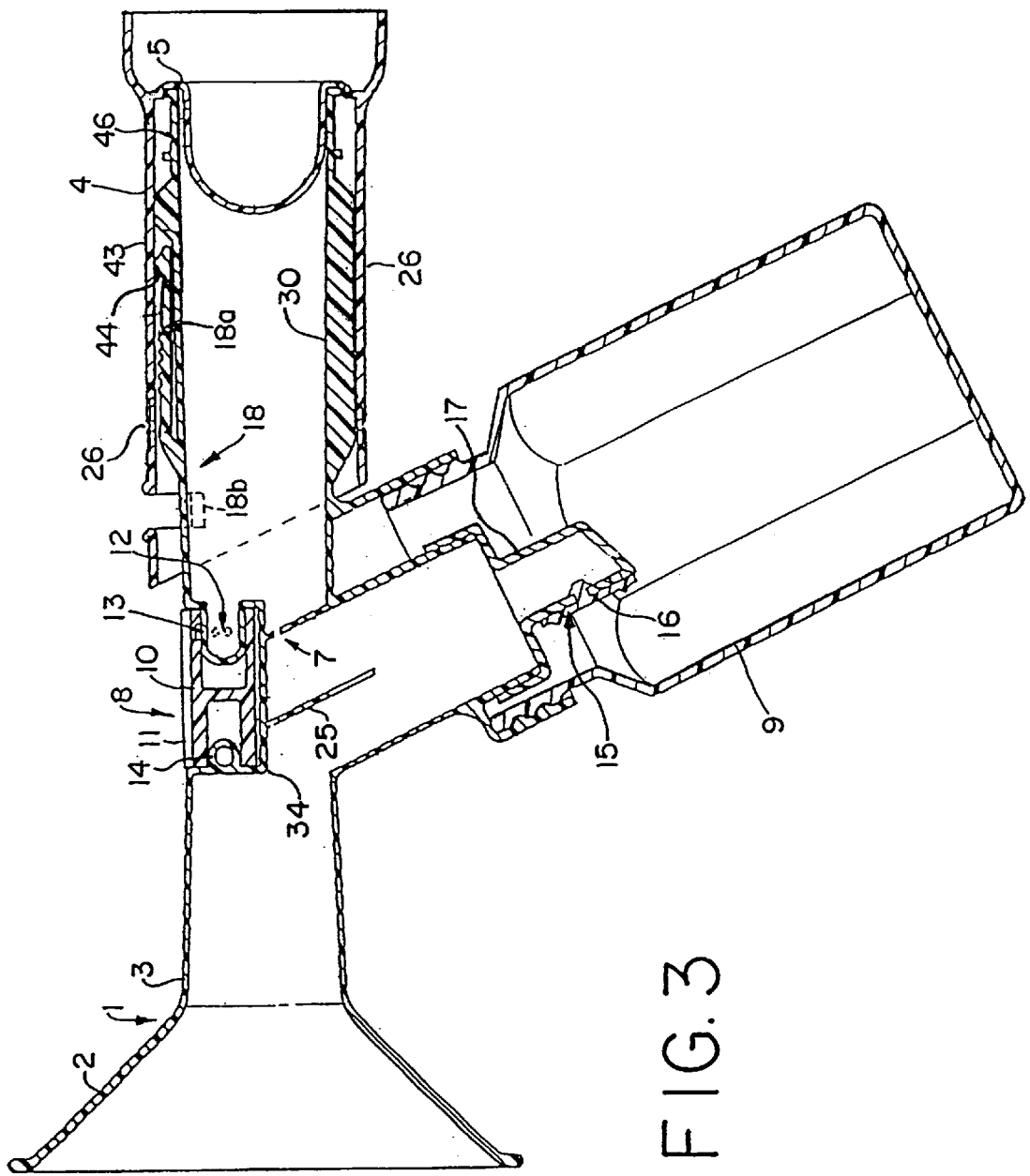
FIG. 3 is a view similar to that of FIG. 2 showing the cylinder in the position of FIG. 1.

When the cylinder 4 is reciprocated to the forward position, i.e., a compression stroke, as depicted in FIGS. 1 and 3, the increased pressure is released, such as through a mechanism as shown and described in U.S. Pat. No. 4,929,229, which is incorporated herein by reference. Vacuum is also released on the rearward stroke through vent hole 26 in the cylinder 4 which is uncovered when the pump reaches the maximum stroke, as depicted in FIG. 3. The pumping action is created by reciprocating the cylinder 4 over the pump tube 30, thereby generating intermittent vacuum that is communicated to the shield 1.

The pump tube 30 is in communication with a collection or catch chamber 6, a vacuum passage 7, and the vacuum regulator 8. The catch chamber 6 extends downwardly from the tubular extension 3, and a container 9 for holding the expressed milk is attachable thereto in a known manner.

A separation wall 25 extends downwardly from the tubular extension and in advance of the vacuum passage 7. The bottom of the separation wall 25 extends below the level of the vacuum passage 7 to block expressed milk flowing from the hood body 1 from entering the vacuum passage 7.

The vacuum regulator 8 modifies the amount of reduced pressure generated by the pumping action. The regulator 8 comprises a rotary member 10 with an internal groove or passage 32 and with plurality of raised bumps 11 (see, e.g., FIG. 4) on the surface of the rotary member having indicia thereon to indicate to the user the vacuum settings. The rotary member 10 has hollow ends. One hollow end encircles a ported structure 13 in the form of a nub that extends out of the front wall of the pump tube 30, having a pair of holes or ports 12. The rotary member 10 fits within a cavity 34 formed in the hood body 1. The ported nub 13 is at one end of the cavity, and a boss 14 is at the other end. The other hollow end of rotary member 10 is received on the boss 14 to rotate thereon. Reduced pressure is adjusted by positioning the internal groove 32 of the rotary member 10 over one, both or neither of ports 12 of the ported nub 13. The internal groove 32 is open to atmosphere. The ports 12 extend into the interior of the hood body 1. Depending upon whether the internal groove 32 is over one port or both ports 12, suction or reduced pressure is thereby modified by allowing air to bleed into the pump tube 30 through the vacuum regulator 8. The regulator 8 is easily rotated, and conveniently located, allowing the user to manipulate it with one finger, if desired.

A valve mechanism 15 is located at the lower portion of catch chamber 6. The valve mechanism 15 is described in U.S. Pat. No. 4,929,229, with a flexible disk 16 mounted to cover openings in a valve housing 17 in a flap-valve fashion. When the breast pump is operated, the disk 16 is caused to close underlying apertures in the valve housing 17 under negative pressure, thus closing the collection chamber 6. When the vacuum is released, milk collected in the collection chamber 6 flows downwardly into the container 9 through the apertures past the disk 16. The valve housing 17 may be attached to the outside of a short tubular extension of the collection chamber 6 via a snug interference fit.

A locking means 18 for preventing the cylinder from accidentally disengaging from the tubular extension is also provided. An angled latch mechanism 18a formed on the pump tube 30 is depicted in FIGS. 2 and 3. The angled latch mechanism 18a has one end integral with the pump tube 30 with a free end that can engage in a groove or slot 18b formed adjacent the open end of the cylinder 4.

FIG. 2 depicts the pump in the position when the cylinder 4 is fully reciprocated toward the rear end of the pump tube 30, i.e., the point of maximum reduced pressure, at which point the angled latch mechanism is engaged in the groove 18b. The latch 18a is resilient, and is biased to engage the inside wall of cylinder 4. The locking means 18 is designed to allow the user to selectively disengage the cylinder 4 from the pump tube 30. A surface 43 of the latch mechanism 18a is angled in ramp-like fashion so that cylinder 4 can slide over the angled latch mechanism 18a when the cylinder 4 is moved over the pump tube 30 to the forward position (compression). The angled latch mechanism 18a also has a vertical edge 44 extending upward at the end of the angled latch mechanism 18a which vertical edge catches in the groove 18b of the locking means 18 to prevent the cylinder 4 from disengaging from the pump tube 30 as the cylinder 4 completes the maximum stroke. Latch 18 can be depressed in the locked position to allow the cylinder to be removed from the pump tube 30.

Figure 5:
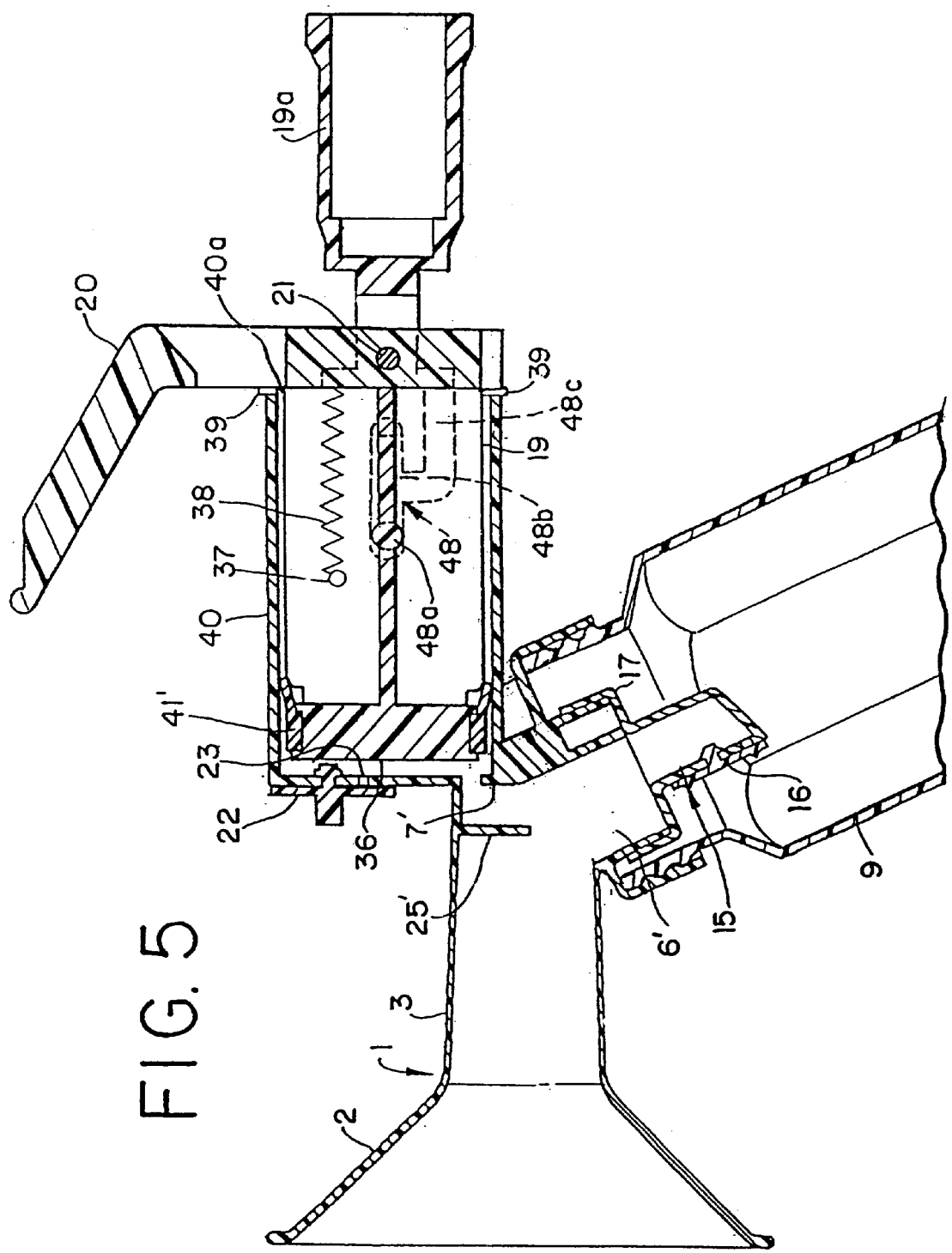
FIG. 5 is a side elevational sectional view of a second embodiment made in accordance with the present invention showing the piston rod in the relaxed or start position.
Figure 6:
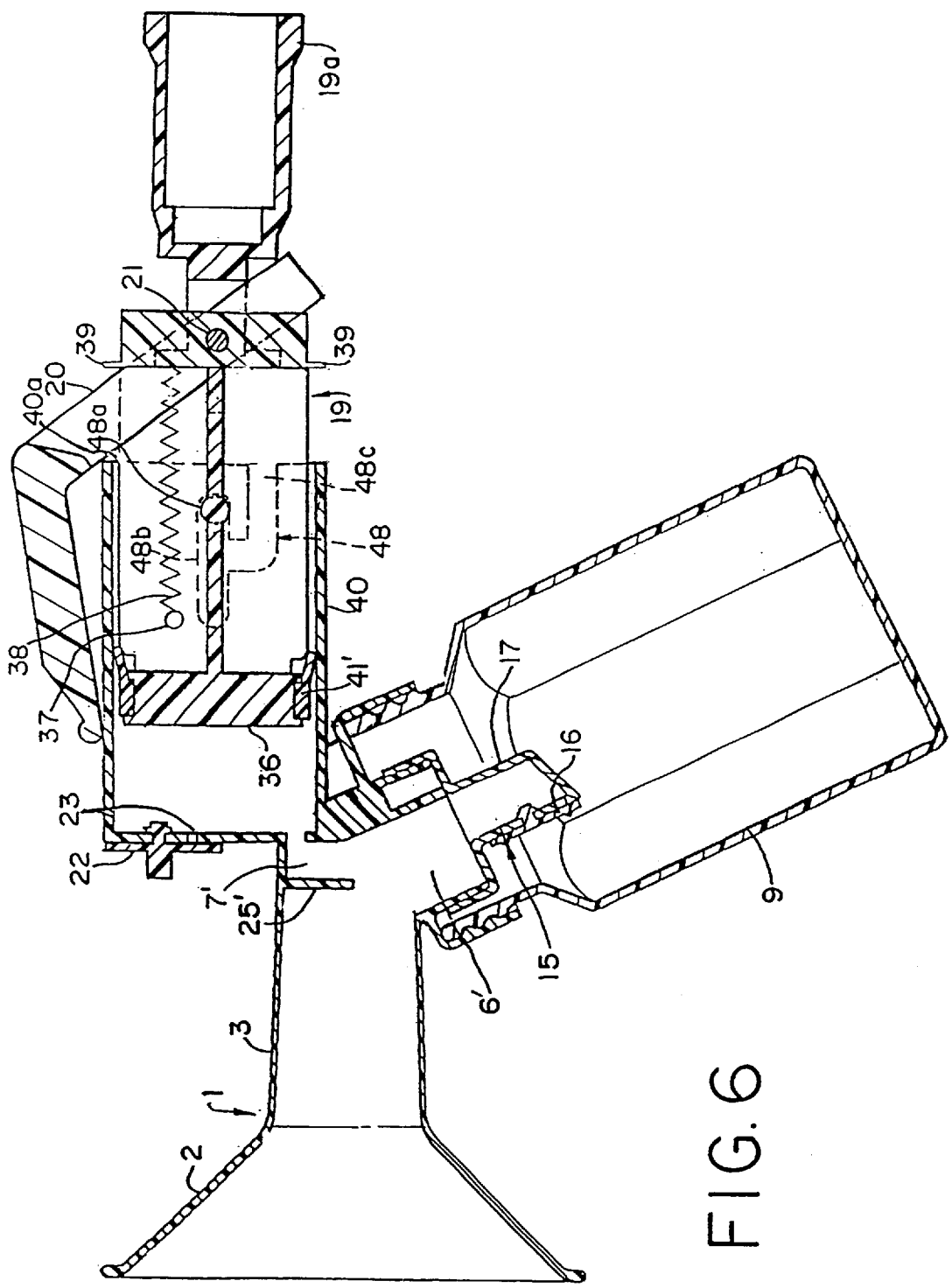
FIG. 6 is a vertical sectional view of the second embodiment showing the position of the lever and the piston rod of the one-hand-operated breast pump when the piston rod is in the position where the maximum amount of reduced pressure is created.

In another embodiment, depicted in FIGS. 5 and 6, the breast pump is designed for one-handed or two-handed operation. It will be noted that in this as well as all embodiments herein, like numbers are used for substantially identical parts. Prime and double prime numbers are used for similar but modified parts.

In this second embodiment, a piston rod 19 has a piston 36 which is reciprocated within a pump cylinder 40. A tubular extension 3 of the hood body 1 in this second embodiment is in communication with a collection chamber 6', a vacuum passage 7', and the cylinder 40. The piston rod 19 is received within the cylinder 40 and creates a vacuum as the piston rod 19 reciprocates the piston 36 within the cylinder 40. A gasket 41' is provided in an annular groove formed around the piston 36 to sealingly engage the interior sidewall of the cylinder 40.

A lever 20 is pivotally mounted on the piston rod 19 via a pin 21. The lever 20 allows the user to operate the pump efficiently and easily using one hand to move the lever 20 to reciprocate the piston rod 19 within the cylinder 40. When the user squeezes the lever 20 from the position of FIG. 5 to a position adjacent or against the cylinder 40, the lever 20 uses the end edge 40a of the cylinder 40 as a fulcrum to move the piston rod 19 outwardly from the cylinder 40, as depicted in FIG. 6, thereby creating reduced pressure within the pump. The lever 20 could be returned to the position in FIG. 5 through manipulation of a handle 19a to push the piston rod 19 back into the cylinder 40, but preferably a spring return can be used to pull the piston rod 19 back to its forward position, fully received within the cylinder 40. The spring return may be located within the cylinder 40 and may comprise a spring 38, one end of which is mounted on a post 37 inside the cylinder 40. The other end of the spring 38 is mounted on a flange 39 extending from the piston rod 19 adjacent the pin 21.

By positioning of the lever 20 in relation to the cylinder 40 so that the pumping action is created by the user closing her hand around the lever 20 and cylinder 40, the pump is ergonomically designed to rely on more correct muscle groups in the user's hand to create and maintain the pumping action. Utilizing the correct muscle groups is important so that the user does not tire or cramp during the pumping process. Fatigue leads to fluctuations in the pumping pressure, which causes ineffective and inefficient pumping.

In this embodiment, an air release flap valve 22 (similar to that in U.S. Pat. No. 4,929,229) covers one or more apertures 23 at the front of cylinder 40 to allow air to escape from the cylinder 40 on the forward (compression) stroke.

A locking means 48 is incorporated into the pump to prevent the piston rod 19 from accidentally disengaging from the cylinder 40 as it is moved toward the open end 40a of the cylinder 40. The locking means comprises a channel 48b on the cylinder 40 in which a pin 48a extending outwardly from the piston travels. The channel 48b allows the piston rod 19 to reciprocate in the manner described. To selectively disengage the piston rod 19 from the cylinder 40, the pin 48a exits through a J-shaped section of channel 48c by aligning the pin with a portion of the J-shaped channel communicating with channel 48b and rotating and then removing the piston rod 19 causing the pin to move through the channel portion 48c.

As in the first embodiment, the collection chamber 6' extends downwardly from the tubular extension 3, and a container 9 for holding the expressed milk is attachable thereto. A separation wall 25' extends downwardly from the tubular extension and in advance of the vacuum passage 7'. The bottom of the separation wall 25' extends below the level of the vacuum passage 7' to block expressed milk flowing from the hood body 1 from entering the vacuum passage 7. Similarly, a valve mechanism 15, preferably of the type and for the purpose described in the first embodiment, is located at the lower portion of collection chamber 6.

This embodiment may also be adapted to utilize a vacuum regulator. For example, a regulator of the type shown in U.S. Pat. No. 4,857,051 may be readily adapted for use with this pump.

One-handed operation of the breast pump of FIGS. 5 and 6 has thus been described. The breast pump is also adapted for two-handed operation, should the user so desire. This is accomplished through the provision of a graspable extension 19a on the piston rod 19. The extension or grip 19a is made for the user to be able to grasp the same and push and pull it to reciprocate the piston 36. Obviously, with a spring-return mechanism such as shown with the lever mechanism 20, the user would simply need to pull the grip formed by the extension 19a, and then allow it to return under influence of the spring 38. Two modes of manually operating the pump are thereby provided.

In a third embodiment of a manually operable breast pump, as shown in FIGS. 7–15, the breast pump has a hood body 1 having two sections: a funnel shaped front section 2 and a tubular extension 3 extending therefrom. Like the first embodiment, a pump tube 30' is in communication with the tubular extension 3 of the hood body 1. A cylinder 4' with end cap 5' is slidably engaged over the pump tube 30'. The end cap 5' herein has an end portion 50 which extends into the cylinder 4' reducing the air space in the cylinder 4' to a desired volume. The end cap 5' can be made removable from the cylinder 4' for cleaning.

When the cylinder 4' is reciprocated to the rear end of the pump tube 30' with an annular groove 46, reduced pressure or vacuum is created. When the cylinder 4', reaches the position of maximum stroke, a vent hole (or holes) 26 is uncovered, releasing the vacuum. The pumping action is created by reciprocating the cylinder 4' over the pump tube 30', thereby generating intermittent vacuum. A flexible gasket ring 41 fits over the rear end of the pump tube 30' in groove 46 to seal the pump tube to the cylinder 4' in a sliding engagement.

The pump tube 30' is in further communication with a collection chamber 6", a vacuum passage 7", and a vacuum regulator 8. The collection chamber 6" extends downwardly from the tubular extension 3, and a container 9 for holding the expressed milk is attachable thereto in a known manner.

A separation wall 25" extends downwardly from the tubular extension and in advance of the vacuum passage 7". The bottom of the separation wall 25" extends below the level of the vacuum passage 7" to block expressed milk flowing from the hood body 1 from entering the vacuum passage 7".

The vacuum regulator 8 (FIG. 7) is positioned on the outer wall of the hood body 1, and specifically in this embodiment, on the outer wall of the tubular extension 3, and functions in the same manner as described in detail in the first embodiment of this invention. Similarly, a valve mechanism 15, preferably of the type and for the purpose described in the first embodiment, is located at the lower portion of collection chamber 6.

In this embodiment, another locking means is used. A post or tooth 27 (FIGS. 9–11) extends downwardly from the top of the inner wall of the cylinder 4' adjacent the front end of the cylinder 4'. As the cylinder is engaged over the pump tube 30', the post 27 is directed into a portion of a J-shaped channel 58c formed on the exterior of pump tube 30'. The post 27 travels along channel 58c, and is then rotated (via the cylinder 4') so that the post 27 can travel into a second channel 58b on the outside of the cylinder. During the pumping action, the post 27 reciprocates within the second channel 58b, which prevents the cylinder 4' from accidentally disengaging from the pump tube 30'. The cylinder 4' can be selectively removed for cleaning by directing the post 27 back out through channel 58c.

A shield insert 42 may be inserted into the funnel-shaped section of the hood body or breast shield 1 of this embodiment, or any of the preceding embodiments. For example, this insert 42 may be of the type used to adapt the breast shield for smaller breasts.

The flexible gasket ring 41 can be placed on the annular groove 46 of the pump tube 30' during extended periods of storage without risk that it may become deformed or take a set, because the diameter of the cylinder 4' is increased slightly in the area at point 45 on the cylinder where the cylinder, when fully engaged over the length of the pump tube 30', would be positioned over the gasket 41 and pump tube 30' during storage.

While the invention has been described with reference to particular embodiments, those having skill in the art will recognize modifications of elements and structure which may facilitate the application of the invention, but which still fall within the scope of the invention. For instance, while this invention has been described in an environment of a breast pump, it could be utilized in other applications.

I claim:

1. A breast pump having two modes of manual operation, comprising:

a hood body for placement over a breast, said hood body having a funnel-shaped portion within which the breast is received;

a pump connecting with said funnel-shaped portion, said pump further comprising a reciprocating element, said reciprocating element in communication with a vacuum chamber said reciprocating element moving along an axis, whereby said reciprocating movement generates an alternating pressure in said vacuum chamber which is communicated to the hood body on the breast to effect expression of milk therefrom;

a first manually operated mechanism mounted to said breast pump for generating said reciprocating movement of said reciprocating element, said first mechanism having a member that is moved by hand in a direction generally radial to said axis during one stroke of said reciprocating movement, and further said first mechanism being operable by the user using one hand to both operate said first mechanism and to maintain said breast pump in position against her breast;

a second mechanism for generating said reciprocating movement of said reciprocating member, whereby said second mechanism moves in a direction generally parallel to said axis during one stroke of said reciprocating movement, and further said second mechanism being sized and shaped to be operable by the user using one hand to operate said second mechanism and another hand to maintain said breast pump in position against her breast; and a container for expressed milk in communication with said funnel-shaped portion, said container being located downstream from said funnel-shaped portion.

2. The breast pump of claim 1, wherein said first mechanism further comprises, a lever pivotally connected to a rod connected to said reciprocating element whereby movement of said lever in a direction generally radial to said axis causes said rod to reciprocate said reciprocating element within said vacuum chamber.

3. The breast pump of claim 2, whereby the starting position of said lever is a distance from said vacuum chamber sufficient to generate negative pressure when said lever is manipulated to generate reciprocating movement of said reciprocating element in said vacuum chamber, but within sufficient proximity of said vacuum chamber to permit the user to grasp both said vacuum chamber and said lever with one hand while maintaining the breast pump in the proper position on her breast with the same hand, said lever being pivotably mounted to said rod and engaging a part of said vacuum chamber as a fulcrum.

4. The breast pump of claim 2, further including a mechanism for returning said lever to a starting position whereby negative pressure is released.

5. The breast pump of claim 1, wherein said second mechanism is an operable part of said reciprocating element, said operable part manipulated by the user and being driven by hand generally along said axis to move said reciprocating element.

6. The breast pump of claim 1, wherein said axis is generally along a longitudinal axis of said funnel-shaped portion.

7. The breast pump of claim 5, wherein said operable part is a grip formed on a rod connected to said reciprocating element, whereby said grip protrudes outwardly from said pump when said rod is fully received within said vacuum chamber.

8. A manually operated breast pump, comprising:

a hood body for placement over a breast, said hood body having a funnel-shaped portion within which the breast is received;

a pumping mechanism connecting with said hood body, said pumping mechanism further comprising a vacuum chamber and a reciprocating element engaged with said vacuum chamber for reciprocating movement occurring along an axis, whereby said reciprocating movement generates an alternating pressure in said vacuum chamber, which when applied to the breast effects expression of milk therefrom;

a lever mechanism mounted to said breast pump for generating said reciprocating movement of said pumping mechanism, whereby said lever mechanism moves in a direction generally radial to the longitudinal axis of the pumping mechanism during a stroke of said reciprocating movement, and further said lever mechanism and said vacuum chamber being graspable by the user using one hand to both operate said lever mechanism and to maintain said breast pump in position against a user's breast;

a lever return mechanism for returning said lever mechanism to a starting position;

one of said vacuum chamber and said reciprocating element having a part sized and shaped to be grasped by a user's hand and manually moved to also generate said reciprocating movement independent of said lever mechanism; and a container for expressed milk in communication with said tubular extension, said container being located downstream from said tubular extension.

9. The breast pump of claim 8, wherein said lever mechanism further comprises a lever pivotally connected to a rod for movement of said lever in a direction radical to said axis during a stroke of said pumping mechanism, whereby said lever causes said rod to travel along said axis of said pumping mechanism in a direction away from the user's breast when said lever is moved toward said vacuum chamber.

10. The breast pump of claim 9, whereby the starting position of said lever is a distance from said vacuum chamber sufficient to generate negative pressure when said lever is manipulated to generate reciprocating movement of said reciprocating element, but within sufficient proximity to said vacuum chamber to permit the user to encircle said lever with the user's fingertips while maintaining contact with said vacuum chamber.

11. The breast pump of claim 10, wherein said lever is pivotally mounted on the rear end of said rod by a pin and engages a part of said vacuum chamber as a fulcrum.

* * * * *

UNITED STATES PATENT AND TRADEMARK OFFICE
CERTIFICATE OF CORRECTION

PATENT NO.     : 6,497,677 B2                                              Page 1 of 1
DATED          : December 24, 2002
INVENTOR(S)    : Brian H. Silver It is certified that error appears in the above-identified patent and that said Letters Patent is hereby corrected as shown below:

Column 8,
Line 46, please replace the word "radical" with -- radial --.

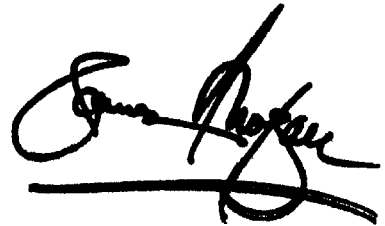

Signed and Sealed this

Twenty-second Day of July, 2003

JAMES E. ROGAN
*Director of the United States Patent and Trademark Office*